United States Patent [19]
Masterson et al.

[11] Patent Number: 5,923,431
[45] Date of Patent: Jul. 13, 1999

[54] SPECTROSCOPIC HELICAL SEPARATOR AND FLUID SAMPLE INTERFACE

[75] Inventors: Brian K. Masterson; Terry R. Todd, both of Placerville, Calif.

[73] Assignee: UOP LLC, Des Plaines, Ill.

[21] Appl. No.: 09/059,788

[22] Filed: Apr. 14, 1998

[51] Int. Cl.[6] .......................... G01N 21/84; G01N 21/90; G01N 33/28; B01D 21/26
[52] U.S. Cl. .......................... 356/426; 356/427; 356/428; 356/70; 356/36; 356/356; 210/787
[58] Field of Search .................. 356/70, 36, 356, 356/426, 427, 228; 210/787, 657, 198.2

[56] References Cited

U.S. PATENT DOCUMENTS

| | | | |
|---|---|---|---|
| 3,813,031 | 5/1974 | Anderson | 233/26 |
| 4,422,941 | 12/1983 | Vaughan, Jr. et al. | 210/657 |
| 4,900,435 | 2/1990 | Anderson | 210/198.2 |
| 5,242,606 | 9/1993 | Braynin et al. | 210/787 |

Primary Examiner—Hoa Q. Pham
Assistant Examiner—Roy M. Punnoose
Attorney, Agent, or Firm—Thomas K. McBride; Frank S. Molinaro; Maryann Maas

[57] ABSTRACT

A spectroscopic fluid sample apparatus for the transmission and detection of radiation with the key components being a housing; a helical bore formed by the housing and extending through the housing for conducting the sample fluid through the bore to induce centripetal acceleration on the sample fluid and establish a radial composition gradient across the sample fluid in the bore; a fluid inlet and a fluid outlet each in fluid communication with the helical bore; and a spectroscopic sample interface in fluid communication with the fluid outlet has been developed.

13 Claims, 2 Drawing Sheets

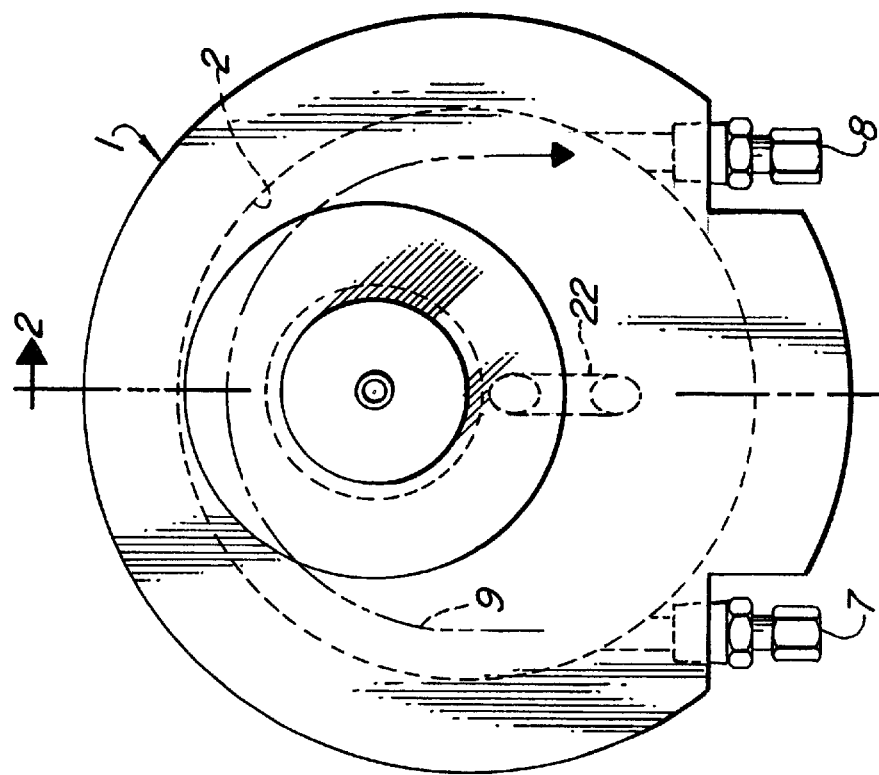
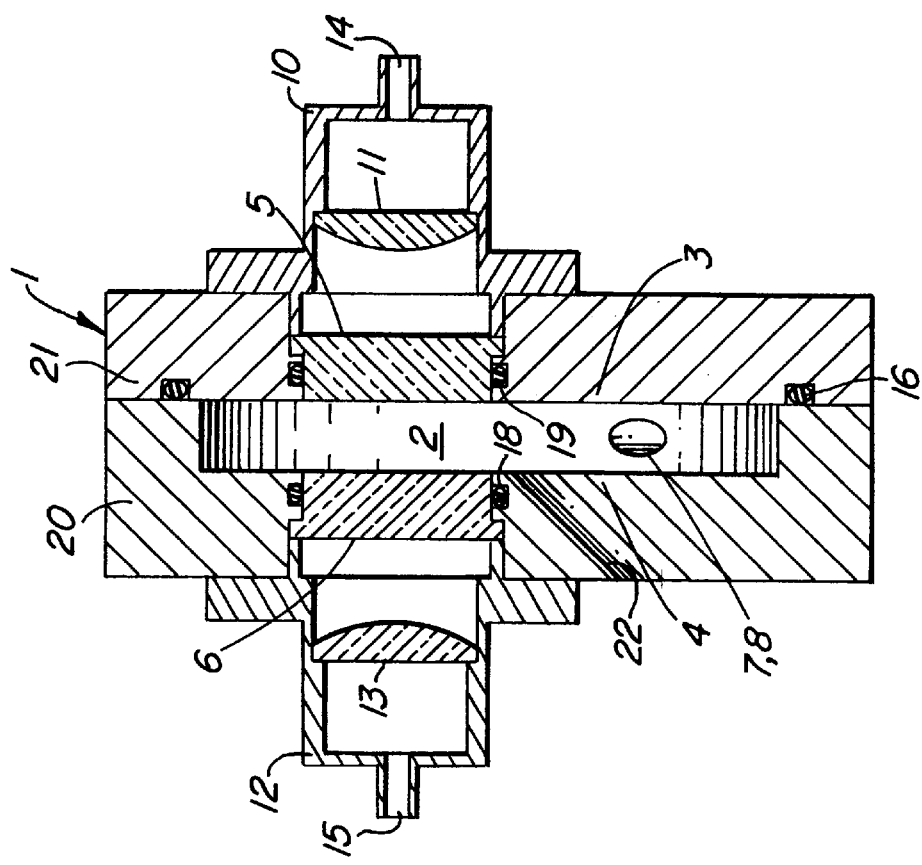

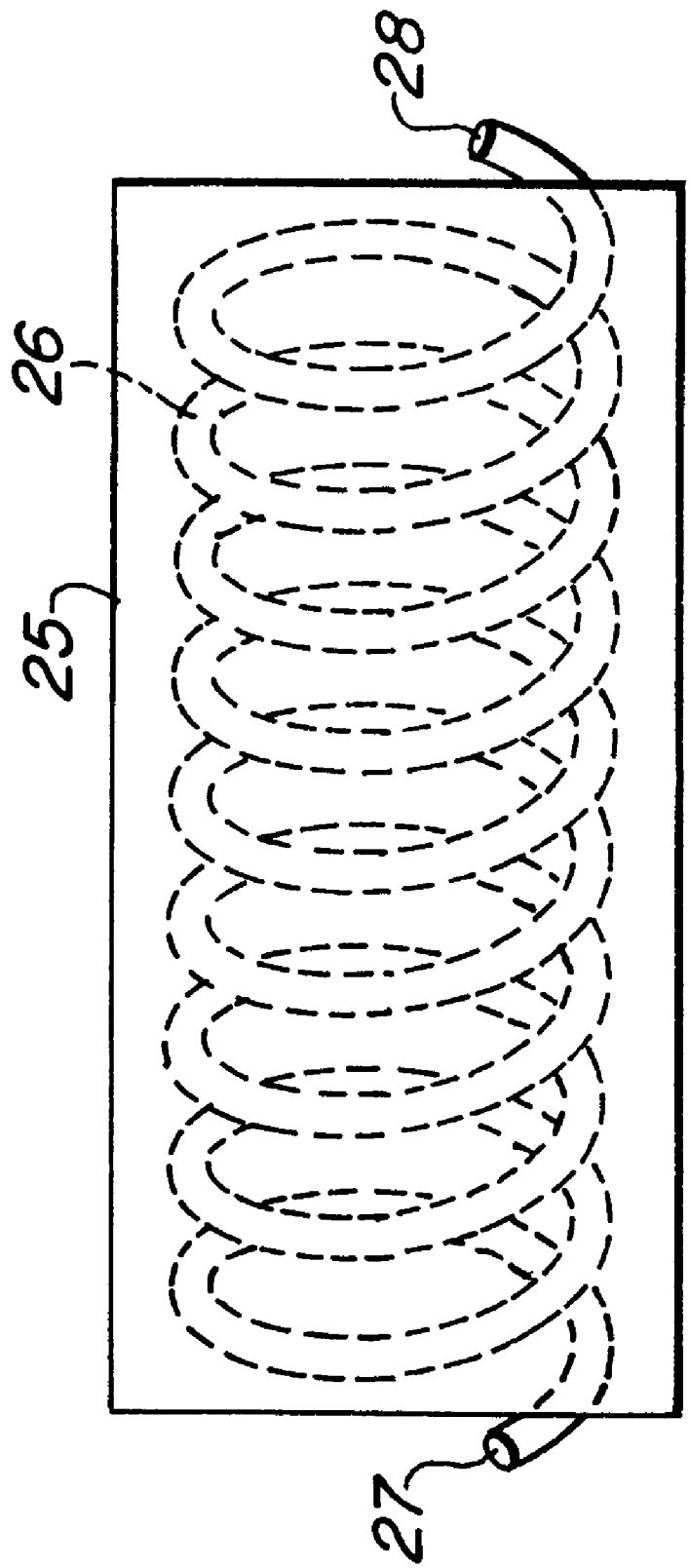

SPECTROSCOPIC HELICAL SEPARATOR AND FLUID SAMPLE INTERFACE

FIELD OF THE INVENTION

The invention relates to a spectroscopic fluid sample apparatus for the transmission and detection of radiation.

BACKGROUND OF THE INVENTION

Instruments for measuring the transmission or absorption of radiation through materials contain five key components: a stable source of radiation, a way to restrict the radiation to select wavelengths of interest, a sample interface, a detector to convert radiation to a measurable signal, and a signal indicator. With fluids, a sample cell may be used as the sample interface to contain the fluid during exposure to the radiation. Such a sample cell must be compatible with the fluid, must provide interface surfaces that are transparent to the radiation, and must be in alignment with the radiation. The sample cell may be located directly in the instrument with each sample being automatically or manually inserted, or the sample cell may be located remotely with radiation being conducted to and from the sample cell. Remote sample cells allow for the radiation to be transmitted or absorbed by the fluid at a position at or near the source of the fluid, thus reducing or eliminating sample transportation and time lag problems.

Absorption spectroscopy requires that the sample of fluid contained within the sample cell be free of impurities or contaminants that would interfere with the radiation transmission or absorption measurements. Problems arise since fluid streams to be analyzed frequently contain such contaminants. For example, it is common to find water, particulates, or other emulsified materials in gasoline. These impurities act as scattering agents that reduce the transmission of radiation through the sample and result in high or noisy baselines that degrade the analytical measurement. Therefore, to effectively use current sample cells with fluids containing such contaminants or impurities, a sample conditioning system must be employed. Typical sample conditioning systems include filters, coalescing filters, membrane separators, adsorbents, and the like. Unfortunately, sample conditioning systems require additional investment and maintenance costs and periodically experience failures. Furthermore, sample conditioning systems may severely restrict the flow velocity of the fluid resulting in excessive lag time and rendering real-time analysis and control impossible.

The present invention provides a fluid sample apparatus that eliminates the need for sample conditioning systems when the base fluid to be measured is distinguishable from the contaminants by a significant difference in density (specific gravity) and is especially useful where the base fluid and the contaminants are in different physical states. The design of the fluid sample apparatus incorporates centripetal acceleration in order to separate materials of different densities, thus permitting interference-free measurement of the lighter or the heavier component. By forcing the fluid sample to travel in a helical path, the less dense components will be forced toward the center of rotation, due to buoyancy, leaving the more dense components farther from the center of rotation. If the measurement is to be made on the more dense components, the radiation is directed to the outer portion of the sample composition gradient, and if the measurement is to be made on the less dense components, the radiation is directed to the inner portion of the sample composition gradient.

SUMMARY OF THE INVENTION

One embodiment of the present invention is a spectroscopic fluid sample apparatus for the transmission and detection of radiation with the key components being a housing; a helical bore formed by the housing and extending through the housing for conducting the sample fluid through the bore to induce centripetal acceleration on the sample fluid and establish a radial composition gradient across the sample fluid in the bore; a fluid inlet and a fluid outlet each in fluid communication with the helical bore; and a spectroscopic sample interface in fluid communication with the fluid outlet. The sample interface may comprise a pair of windows aligned along a common axis intersecting a portion of the fluid outlet, and a retainer may hold a collimating lens and optical fiber adjacent each window.

Another embodiment of the invention is one where the sample interface comprises a spectroscopic fluid sample cell for the transmission and detection of radiation with the key components being a housing; a centripetal acceleration chamber formed by the housing and extending through the housing for circulating a fluid through the housing over a curvilinear flow path about a rotational axis; a pair of windows aligned along a common axis intersecting a portion of the chamber and parallel to the rotational axis; a fluid inlet and a fluid outlet in communication with the centripetal acceleration chamber; and a flow director positioned in the housing to induce centripetal acceleration on fluid passing through the chamber and establish a radial composition gradient across the fluid chamber. A retainer may hold a collimating lens adjacent each window, and an optical fiber may be used to conduct the radiation to the sample cell with a second collimating lens and optical fiber to conduct the sample-altered radiation away from the sample cell. The windows may be coaxial with the cylindrical bore or may be positioned acentrically within the diameter of the cylindrical bore. The axis of alignment of the pair of windows is parallel with the rotational axis of fluid within the centripetal acceleration chamber.

Yet another embodiment of the invention is to provide a method of measuring the transmission or absorption of radiation by at least one separated or partially separated component of a fluid sample by flowing the fluid sample through a helical bore to cause centripetal acceleration of the fluid within the bore; separating, at least partially, within the helical bore by buoyancy forces, at least one component from at least one other component having a different density to establish a radial composition gradient across the fluid in the bore; flowing at least a portion of the fluid from the bore to a spectroscopic sample interface; directing radiation through the spectroscopic sample interface and the fluid; and measuring the change in the radiation passed through the fluid. A more specific embodiment of the above embodiment is one where the fluid flowing from the helical bore to the spectroscopic sample interface is flowed through a centripetal acceleration chamber at a velocity and a direction to cause centripetal acceleration of the fluid within the chamber to maintain or increase the separation of at least one component from at least one other component having a different density, directing the radiation through the chamber so that the radiation passes through one of the separated or at least partially separated components; and monitoring the change in the radiation after passing though the separated or partially separated component.

BRIEF DESCRIPTION OF THE DRAWINGS

FIG. 1 is an end view of a fluid sample cell located between two sets of lenses and optical fibers.

FIG. 2 is a section view of the fluid sample cell taken across line A—A of FIG. 1.

FIG. 3 is a view of a housing defining a helical bore having a fluid entry and a fluid exit.

DETAILED DESCRIPTION OF THE INVENTION

In general terms, the invention is a spectroscopic helical separator and sample interface where the helical separator is a helical bore defined by a housing and having a fluid inlet and a fluid outlet in fluid communication with the helical bore. The sample flowing through the helical bore is at least partially separated by centrifugal forces and the spectroscopic sample interface allows radiation transmission or absorption measurements to be performed on at least one of the separated components. The sample interface may be a fluid sample cell designed to maintain the separation or to further separate components of different densities within the cell using centrifugal force, thereby allowing radiation transmission or absorption measurements to be performed on at least one of the separated components. The details below first discuss a preferred sample cell focusing on the hardware of the fluid sample cell and not on the optics required for measurements. For example, to perform remote radiation transmission or absorption measurements, additional apparatus such as collimating lenses and optical fibers may be used in conjunction with the cell, but since many lenses and optical fibers are known in the art and the selection of a specific lens or optical fiber is not critical to the success of the invention, the lenses and optical fibers will not be described in great detail here. Similarly, the spectrometers used in conjunction with the fluid sample cell will not be discussed. It should be noted, however, that the fluid sample cell may be located in a variety of positions including in a remote sampling device or within a spectrometer itself.

A fundamental requirement of the sample cell is a centripetal acceleration chamber that provides a substantially curvilinear path for the circulating sample fluid. Suitable chambers for centripetal acceleration may be provided by a variety of chamber forms. For example, frusto-spherical, frusto-conical, or modified toriodal shapes can all provide a central axis about which the sample fluid may revolve to induce an acceleration that will produce a radial composition gradient through sample components. Cylindrical forms are particularly preferred and include elements defined by continuous curves as well as rectilinear shapes such as polygons having sufficient sides to provide the substantially curvilinear path necessary for inducing the necessary centripetal acceleration. For convenience, this invention is described in the context of the preferred cylindrical bore, which description is not meant to exclude other arrangements for the centripetal acceleration chamber.

The cylindrical bore is defined by a housing. The housing is constructed of material compatible with the fluid sample to be analyzed. Typical examples of the housing material include stainless steel and other corrosion-resistant steels as well as polymers and the housing material selected depends on the application. The exterior shape of the housing is not critical. In the preferred case, the housing defines a cylindrical bore having two ends and a circumference. The size of the bore also depends on the application which will be discussed further below. To facilitate forming the bore, the housing may be formed of at least two pieces. Seals such as o-rings may be used to seal the space between the multiple housing sections.

Adjacent each end of the cylindrical bore is a window. The windows may be composed of any material compatible with the fluid sample having appropriate radiation transmission such as sapphire, quartz, glass, and polymers. The shape of the window is not critical, and the positioning of the windows across the ends of the cylindrical bore depends on the application, as discussed below. The windows are aligned along a common axis parallel to the axis of the cylindrical bore and may be sealed to prevent fluid leakage.

A fluid inlet and at least one fluid outlet are in communication with the cylindrical bore to allow fluid sample to pass continuously through the sample cell. In a preferred embodiment, the positioning of the inlet is important to the success of the invention. The fluid inlet is positioned so that the stream of fluid entering the cylindrical bore enters tangentially to the curvilinear flow path of the sample. Similarly, the fluid outlet may be positioned so that the stream of fluid exiting the cylindrical bore exits tangentially to the curvilinear flow path of the sample. However, the positioning of at least one outlet may vary as shown below. The velocity and initial direction of the fluid sample stream along with the cylindrical shape of the bore operate to create rotation of the fluid within the bore. Alternately, the fluid inlet may be positioned other than tangentially to the curvilinear flow path of the sample, and a flow director such as vanes or grooves may be incorporated into the cylindrical bore to induce the rotation of the fluid within the bore. The rotation creates centrifugal force and the centrifugal force operates to move all the components of the sample stream outward towards the wall of the bore. Differences in density cause the less dense materials to be buoyed radially inward while the denser materials remain along the cylinder bore. A separation is effected with the more dense components in an outer ring along the circumference of the cylindrical bore and the less dense components in the interior portion of the cylindrical bore. For example, upon entering the sample cell, the flow of a gasoline stream containing particulates and water will be forced to angularly rotate along the circumference of the housing. The denser water and particulates will remain along the outer portion of the cylindrical bore as the gasoline is buoyed inward, now free of contaminants. The windows may be positioned so that radiation is passed through only the inner portion of the sample cell where the contaminant-free gasoline is contained. Note, however, that the exact center of rotation is not usually the preferred location for the radiation transmission or absorption measurements. A vortex, bubbles, or stagnant fluid may be at the center of rotation interfering with accurate measurements. In this gasoline example, positioning the window and directing the radiation slightly off the center of rotation is preferred.

The sample cell may be used in a variety of applications as long as the components to be separated have sufficiently different densities, i.e., the densities of the components to be separated must be sufficiently different so that the centrifugal forces of the chosen cell design are strong enough to perform the necessary degree of separation. The cell design may be modified to increase the centrifugal forces, but the densities of the components must not be so similar that even maximum centrifugal forces are insufficient to perform the separation. Note that depending upon the application, a partial separation of at least one component may be all that is required. The centrifugal forces may result in only a gradient of components, but such a gradient may be sufficient for the optical measurements being performed. If the denser material is the undesirable impurity, then the desired material can be optically measured near the center of the cell without interference from the impurities such as when measuring gasoline in a stream containing gasoline, particulates, and water. Conversely, lighter impurities may be separated from heavier desired material with the sample measurements being performed near the circumference of the cylindrical bore, such as when separating bubbles from a liquid. The sample cell of the invention is particularly suited for use with low viscosity fluids containing impurities of a different phase. Of course, the sample cell will not operate to effectively separate soluble liquids from each other.

The difference in the densities of the components to be separated and the general nature of the centrifugal-based separation may cause a problem. The lighter components having been buoyed inward may become trapped by the layer of higher density materials and become stagnant and perhaps build up over time. Solutions to this problem depend on the relative flow rates and densities of the components being separated. The most elegant solutions rely on keeping the components apart once they have been separated.

Dual or multiple outlets in fluid communication with the cylindrical bore and equipped to allow independent adjustment of the relative flow rates of each output stream would allow the denser materials to be removed from the circumference of the cylinder, while the less dense materials are removed from the central portion of the cylinder. Therefore, one outlet is positioned at a more central position within the cylindrical bore relative to that of another outlet. By adding the centrally located additional outlet, each stream resulting from the separation is allowed to exit the sample cell without re-mixing. The centrally located outlet becomes particularly important when measuring the denser component. With only one outlet, the less dense component must cross the component of greater density and thus contaminate it in order to exit the sample cell, or the less dense component may collect in sufficient volumes to completely displace the denser component resulting in the wrong component being measured. If desired, the two or more separated streams in the outlets could then be recombined outside the sample cell after the transmission or absorption measurement has been made. The modified two- or multiple-outlet designs, while general in nature, would allow the sample cell to be configured for the specific fluid stream under analysis.

Incorporating physical separators such as semi-permeable membranes or filters into the sample cell is another solution. For physical separators to be successful, the components to be separated must have a property other than density that differentiates them. The physical separator takes advantage of this additional property to act as a one-way valve preventing the separated components in the sample cell from recombining. Care must be taken in placing the physical separator such that the buoyancy process used to separate the components is not compromised due to the one-way nature of the device. A common example of such a physical separator is a hydrophobic filter. Modifications such as multiple outlets and physical separators, while not central to the invention, may provide additional capability to separate and analyze streams of similar density.

As mentioned earlier, the size of the cylindrical bore is dependent upon the application. The centripetal acceleration, a, of a rotating object is given by $a=v^2/r$ where v is the tangential velocity and r is the radius. To maximize the acceleration and hence the separation force, a high velocity and a small radius are most preferred. However, realities such as the viscosity of the sample, the density differences of the components to be separated, turbulence, and the time required to separate the components under the applied stress must be considered in determining the optimum size of the cylindrical bore and the velocity of the fluid sample. Such determinations are readily accomplished using modern fluid dynamic software such as Fluent™ from Fluent Inc. (Lebanon, N.H.), Adina® from Adina R&D Inc. (Watertown Mass.), and CFD Two-Phase™ from CFD Research Corporation (Huntsville, Ala.).

The simplest fluid flow path through the cell is where the sample enters the cylindrical bore tangentially to the diameter of the cylindrical bore and follows a U-shaped path through the sample cell exiting the cylindrical bore on the opposite side, tangentially to the diameter of the cylindrical bore. The flow path would be analogous to the U-shape of a 180 degree tube bend. A modified flow pattern is possible by positioning the inlet and outlets so that the fluid traverses 270 degrees of rotation before exiting.

If the sample to be analyzed is viscous, more time or work in the cell may be required for the sample to separate. A helical or corkscrew-like flow pattern may be used, or the radius of the cylindrical bore may be decreased to increase the separation efficiency through time and force, respectively. Additionally, the cross-section of the flow path could be varied by starting with a square or circular pattern and gradually changing to a rectangular pattern with the long dimension along a radius of the cylindrical bore. Changing the aspect ratio (width of the passageway to height of a passageway in a helical flow path) allows greater differentiation of density as well as a means to accommodate different optical measurement path lengths.

For difficult separations, a second housing defining a helical bore may be placed in fluid communication with a spectroscopic sample interface. The same principles and forces described above regarding the cylindrical bore operate within the helical bore to provide a radial composition gradient across the sample fluid in the helical bore. The second housing and helical bore are sized to provide the necessary time or work for the separation. The separated or partially separated components exiting the helical bore are introduced to a spectroscopic sample interface which may be any of those commonly known in the art. It is important, however, that the separation of components achieved in the helical bore be maintained. Therefore, it is preferred that the separated components exiting the helical bore are immediately introduced to the cylindrical bore of the above-described sample cell via the fluid inlet to the cylindrical bore and the centrifugal motion in the cylindrical bore is used to maintain and perhaps increase the separation of the components while transmission or absorption measurements are conducted.

Alternately, the sample interface may be a pair of windows aligned along a common axis and intersecting a portion of the fluid outlet. At least one retainer, affixed to the fluid outlet, may hold a collimating lens in stationary alignment with each window and an optical fiber in stationary alignment with each collimating lens. To perform a measurement, the radiation would be directed to that portion of the radial composition gradient containing the component of interest. In another embodiment, the fluid outlet may contain at least two fluid conduits with each fluid conduit conducting a different portion of the composition gradient of the fluid and at least one of the fluid conduits being in fluid communication with the spectroscopic sample interface.

Without intending to limit the scope of the invention, and as merely descriptive, the invention is described below in terms of a specific embodiment. Optics such as collimating lenses and optical fibers are discussed merely to illustrate the apparatus as it might be used in one specific device and are not meant to limit the scope of the invention in any way. For ease of understanding, the invention is described where the spectroscopic sample interface is a sample cell having a cylindrical bore with the most simplistic fluid flow pattern, the U-shaped pattern.

FIG. 1 generally shows the fluid sample cell. The cell has housing 1 defining internal cylindrical bore 2. Inlet 7 and outlet 8 are positioned to help define sample flow path 9. Optional second outlet 22 is shown in fluid communication with the central portion of cylindrical bore 2.

FIG. 2 shows the internal arrangement of the sample cell in more detail. An O-ring seal 16 surrounds bore 2 and seals the space between the two pieces of housing 1, the housing cup 20 and housing cover 21 together when clamped by suitable means (not shown). Cylindrical bore 2 has a cover end 3 and a cup end 4. Cover window 5 is adjacent cover end 3, and cup window 6 is adjacent cup end 4. Windows 5 and 6 are axially aligned across bore 2 parallel to the axis of rotation within bore 2 and having space of the cylindrical bore between them. O-ring seals 19 and 18 seal space around windows 5 and 6, respectively, from fluid leakage. A cup retainer 10 fixes an optical fiber 14 and collimating lens 11 adjacent to housing cup 20 and in alignment with window 5. Similarly, a cup retainer 12 fixes an optical fiber 15 and a collimating lens 13 adjacent housing cover 21 and in alignment with window 6.

Sample separations and measurements are performed by continuously introducing the sample fluid via inlet 7 into cylindrical bore 2 and removing the sample fluid via outlet 8. The velocity of the fluid and the cylindrical shape of the bore establishes a flow path that causes centrifugal motion of the sample. Buoyancy forces drive the less dense material to the inner portions of cylindrical bore 2. More dense material remains along the circumference of cylindrical bore 2. Windows 5 and 6 are positioned to allow radiation to pass through the desired separated material which, in the figures, is the less dense material. Thus, windows 5 and 6 are positioned in optical alignment with each other with one window adjacent each end of the cylindrical bore along a radius of the bore and slightly off the center of rotation of the fluid sample. To make a transmission or absorption measurement, radiation from a spectrometer is conducted via an optical fiber, 14, to the sample cell and directed through a collimating lens, 11, through the separated less dense material of the fluid sample, through a second collimating lens, 13, and into the other optical fiber, 15. The sample altered radiation is conducted back to the spectrometer for interpretation. If the more dense material was to be the subject of the measurements, the windows, lenses and optical fibers would be located near the circumference of the cylindrical bore. If more than one separated component were to be measured, multiple windows and optics could be employed on the same sample cell, or a single set of optics could be moved to multiple positions.

FIG. 3 shows a housing 25 surrounding a helical bore 26 which has a fluid inlet 27 and a fluid outlet 28. Fluid outlet 28 is in fluid communication with inlet 7 of the sample cell. A sample requiring additional separational forces is introduced to helical bore 26 via fluid inlet 27 and flowed through helical bore 26 to induce centrifugal motion of the sample resulting in buoyancy forces driving the less dense material to the inner portions with the more dense material remaining along the outer surface of the helical bore 26. The partially separated sample exits through fluid outlet and is conducted into the sample cell discussed above via inlet 7. Continued separation and measurement of the sample is conducted as described above.

It must be emphasized that the above description is merely illustrative of a preferred embodiment of the invention and is not intended as an undue limitation on the generally broad scope of the invention. Moreover, while the description is narrow in scope, one skilled in the art would understand how to extrapolate to the broader scope of the invention. For example, positioning the windows so that the more dense separated component is exposed to the radiation, sizing the cylindrical bore and positioning the inlet and outlets to form a helical fluid flow path, retaining the fluid flow cell within a spectrometer, and using other commonly known spectroscopic sample interfaces can all be readily extrapolated from the foregoing description.

What is claimed is:

1. An apparatus for the separation of components in a sample fluid and the transmission and detection of radiation comprising:

a) a housing;

b) a helical bore formed by the housing and extending through the housing for conducting the sample fluid through the bore to induce centripetal acceleration on the sample fluid and establish a radial composition gradient across the sample fluid in the bore;

c) a fluid entry and a fluid exit each in fluid communication with the helical bore; and d) a spectroscopic sample interface in fluid communication with the fluid outlet.

2. The apparatus of claim 1 wherein the spectroscopic sample interface comprises a pair of windows aligned along a common axis intersecting a portion of the fluid exit.

3. The apparatus of claim 2 further comprising at least one retainer, affixed to the fluid exit, and holding a collimating lens in stationary alignment with each window and an optical fiber in stationary alignment with each collimating lens.

4. The apparatus of claim 1 wherein the fluid exit comprises at least two fluid conduits, each fluid conduit conducting a different portion of the radial composition gradient, and at least one fluid conduit in fluid communication with the spectroscopic sample interface.

5. The apparatus of claim 1 wherein the spectroscopic sample interface is a fluid sample cell comprising:

a) a cell housing;

b) a centripetal acceleration chamber formed by the cell housing and extending through the cell housing for circulating fluid through the cell housing over a curvilinear flow path about a rotational axis;

c) a pair of windows aligned along a common axis intersecting a portion of the chamber and parallel to the rotational axis;

d) a fluid inlet in communication with the chamber;

e) a fluid outlet in communication with the chamber; and f) a flow director positioned in the housing to induce a centripetal acceleration on the fluid passing through the chamber and establish a radial composition gradient across the fluid in the chamber.

6. The apparatus of claim 5 wherein the cell housing defines a flow director that communicates the fluid from the inlet into the chamber along a flow path tangential to the curvilinear flow path of the fluid in the chamber.

7. The apparatus of claim 5 further comprising at least one retainer, affixed to the cell housing, and holding a collimating lens in stationary alignment with each window and an optical fiber in stationary alignment with each collimating lens.

8. The apparatus of claim 1 wherein the spectroscopic sample interface is a fluid sample cell comprising:

a) a cell housing;

b) a centripetal acceleration chamber formed by the cell housing and extending through the cell housing for circulating a fluid through the cell housing over a curvilinear flow path around a rotational axis;

c) a pair of windows aligned along a common axis intersecting a portion of the chamber and parallel to the rotational axis;

d) a fluid inlet in communication with the chamber and positioned tangentially to the curvilinear flow path to induce centripetal acceleration on the fluid passing through the chamber and establish a radial composition gradient across the fluid in the chamber; and e) at least one fluid outlet in communication with the chamber.

9. The apparatus of claim 8 further comprising at least one retainer, affixed to the cell housing, and holding a collimating lens in stationary alignment with each window and an optical fiber in stationary alignment with each collimating lens.

10. A method of measuring the transmission or absorption of radiation by at least one separated component of a fluid sample comprising:

a) flowing the fluid sample through a helical bore to cause centripetal acceleration of the fluid within the bore;

b) separating, at least partially, within the helical bore by buoyancy forces, at least one component from at least one other component having a different density to establish a radial composition gradient across the fluid in the bore;

c) flowing at least a portion of the fluid from the bore to a spectroscopic sample interface;

d) directing radiation through the spectroscopic sample interface and the fluid; and e) measuring the change in the radiation passed through the fluid.

11. The method of claim 10 wherein the components to be separated are of different phases.

12. The method of claim 10 wherein the fluid sample is gasoline containing particulates and water.

13. The method of claim 10 further characterized in that the fluid sample is flowed through a chamber of the spectroscopic sample interface at a velocity and a direction to cause centripetal acceleration of the fluid thereby maintaining the separation or further separating at least one component from at least one other component.

* * * * *